US00PP18509P3

(12) United States Plant Patent

Hanna et al.

(10) Patent No.: US PP18,509 P3

(45) Date of Patent: Feb. 26, 2008

(54) *PENNISETUM PURPUREUM* PLANT NAMED 'PRINCE'

(50) Latin Name: *Pennisetum purpureum*
Varietal Denomination: Prince

(75) Inventors: Wayne W. Hanna, Chula, GA (US); John M. Ruter, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 117 days.

(21) Appl. No.: 11/151,586

(22) Filed: Jun. 13, 2005

(65) Prior Publication Data

US 2006/0282928 P1 Dec. 14, 2006

(51) Int. Cl.
*A01H 5/00* (2006.01)

(52) U.S. Cl. ..... Plt./384

(58) Field of Classification Search ..... Plt./384
See application file for complete search history.

(56) References Cited

PUBLICATIONS

J. M. Ruter; Breeding, Evaluation, and Production of New Nursery Crops; University of Georgia, Horticulture, Athens, Georgia; Award Information Including Summary, Objectives, and Approach Posted Jun. 28, 2005; Progress Update Posted Mar. 14, 2006.*

* cited by examiner

*Primary Examiner*—Kent Bell
(74) *Attorney, Agent, or Firm*—Greenlee Winner and Sullivan, P.C.

(57) ABSTRACT

*Pennisetum purpureum* 'Prince' is a semi-dwarf, purple-foliaged napiergrass. It is a perennial in USDA hardiness zones 8–10, and a vigorous annual in more northern zones.

1 Drawing Sheet

Botanical designation: *Pennisetum purpureum* (L.) Schum. 'Prince'.

BACKGROUND OF THE INVENTION

The present invention relates to a new and distinct cultivar of *Pennisetum purpureum,* commonly called napiergrass, hereinafter referred to by its cultivar name 'Prince'. This cultivar is grown primarily as an ornamental for landscape use, and for use as a potted plant.

Seeds of two napiergrass accessions, designated Anae Roxo CNPGL, were received from CENARGEN/EMBRAPA in Brazil in April 1996. These were grown under quarantine in the greenhouse during the winter of 1996-97. They segregated for a wide variety of green and various shades of purple plants with a range of vigor. The most vigorous purple pigmented plant in each accession, given the Tifton numbers N240 and N241, were selfed. Seeds of these plants were planted in the field in 1997. The progenies from these selfed plants again segregated for color and vigor in the field. Three vigorous plants, from each accession, with different shades of purple pigment development were vegetatively propagated for further evaluation in a napiergrass maintenance nursery in 1998. In 1999, two accessions, N241-5 (dwarf) and N241-8 (semidwarf) were selected for further evaluation.

In 1999, multi-plant observation plantings were made at Tifton (USDA Zone 8a). Replicated tests were planted in 2000 at Blairsville (USDA Zone 6b), Griffin (USDA Zone 7b), and Savannah (USDA Zone 8b). Plantings were made at Tifton in 2001 and 2003. All test sites except Tifton were irrigated. Plants in Blairsville and Griffin did not recover in 2001 following temperatures as low as −17° C. Plants in Tifton and Savannah survived when exposed to low temperatures of −6° C. and −8° C., respectively.

In 2003 the name 'Prince' was assigned to N241-8.

'Prince' has been asexually propagated at Tifton by stem cuttings since 2002. Stem cuttings with two nodes tended to produce the most shoots, although somewhat reduced in vigor, based on three-week plant heights. The characteristics of the cultivar have been stable and reproduced true to type in successive vegetative generations.

'Prince' has been compared to *Pennisetum setaceum* 'Rubrum' (unpatented) and to *Pennisetum purpureum* 'Princess' (U.S. Plant patent application Ser. No. 11/151,587). The 'Prince' plant is almost twice as high as 'Rubrum' and 'Princess'. 'Prince' has a similar base circumference and similar number of tillers to 'Princess', but has almost twice the top canopy spread (diameter of arching leaves at top of plant). The 'Prince' plant has a much greater base circumference, top canopy spread, and more than twice the number of tillers as 'Rubrum'. 'Prince' has significantly longer leaves that 'Princess' and 'Rubrum', with similar leaf width to 'Princess', but much wider than 'Rubrum'.

SUMMARY OF THE INVENTION

'Prince' has not been observed under all possible environmental conditions, and the phenotype may vary somewhat with changes in light, temperature, soil, and rainfall without, however, any variance in genotype.

The following traits have been observed and represent the characteristics of the new cultivar. In combination these characteristics distinguish 'Prince' from other varieties in commerce known to the inventors.

1) Greater plant height and top canopy spread than 'Princess' and greater height, plant circumference and tiller number than 'Rubrum'.

2) Longer leaf length than 'Princess' and greater leaf length and width than 'Rubrum'.

3) Greater vigor under irrigated conditions than 'Rubrum'.

4) Greater cold hardiness (USDA Zone 8) than 'Rubrum'.

BRIEF DESCRIPTION OF DRAWINGS

The accompanying illustration shows characteristics of the new cultivar in a photograph as true to color as is reasonable to make in illustrations of this nature.

BOTANICAL DESCRIPTION OF THE PLANT

Figure 1:
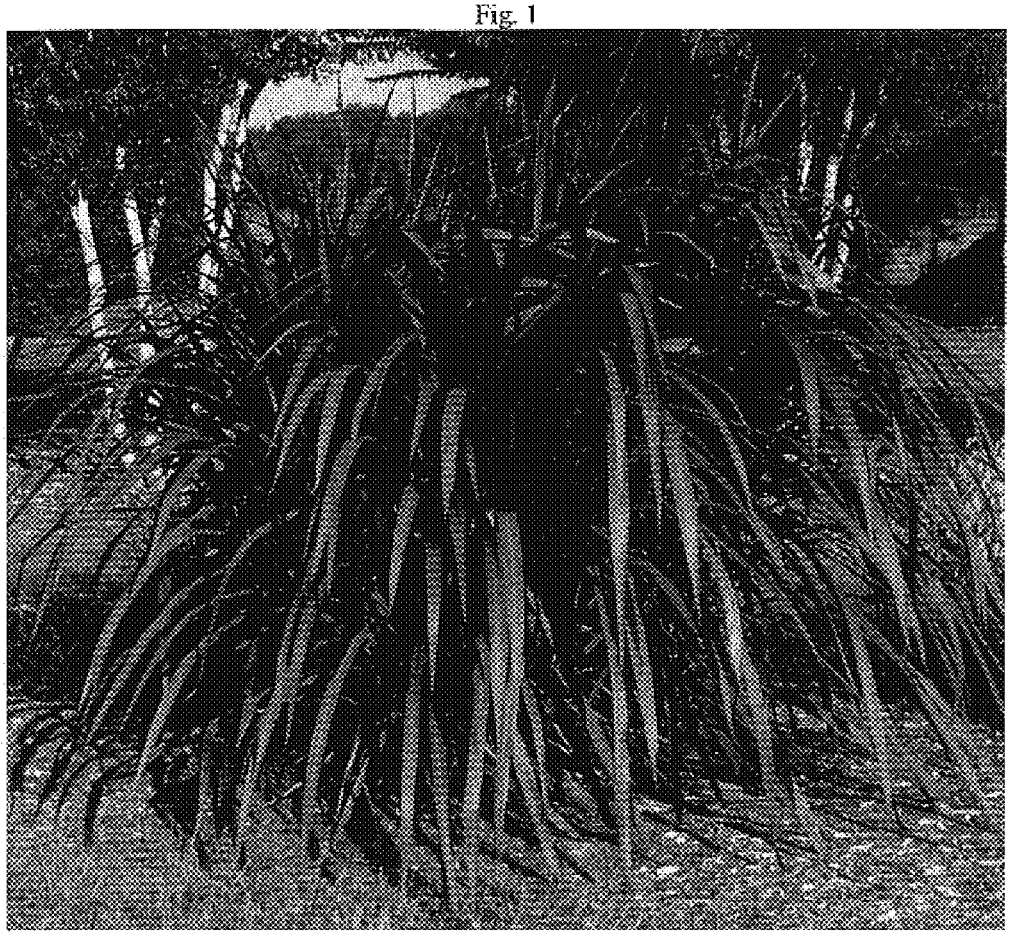
FIG. 1. A two-year-old plant growing in full sun in the ground at Savannah, Ga. (Aug. 1, 2002). The plant is 218 cm high, with a base circumference of 371 cm.

A detailed description of 'Prince' follows. Colors are based on The Royal Horticulture Color Chart, 2001 edition. Measurements/characteristics were taken from one, two, and three-year-old plants grown in the ground under full sun at Tifton, Ga. (USDA Zone 8a ). Measurements are the average of 5 to 10 samples.

Classification:

*Botanical*—'Prince' is a cultivar of *Pennisetum purpureum.*

*Parentage.*—Seed from unkonwn napiergrass accessions.

*Propagation.*—Vegetatively by stem cuttings.

Plant: The plant is perennial in USDA hardiness zones 8–10, and can be grown as a vigorous annual in more northern zones.

*Size.*—The height of the plant ranged from 94 to 200 cm under different environmental conditions, with an average height of 159 cm. The base circumference ranged from 66 to 259 cm, with an average of 157 cm, with 20 to 91 tillers, averaging 52. The top canopy spread, or diameter of arching leaves at the top of the plant ranged from 138 to 259 cm, with an average of 186 cm.

*Vigor.*—The plant is quite vigorous, and produced 40 tillers in one year under non-irrigated conditions, and twice that number of tillers under irrigated conditions.

Two or three node cuttings with foliage removed root well in 8.3 cm liner pots, with rooting percentages in excess of 90%. Well rooted liners shifted from 8.3 cm pots to #5 (19.0 liter) containers in mid-April produced salable plants at a commercial nursery in 40 days. After cutting back, plants were again salable after 57 days. In 19 liter containers using a pine bark-based substrate, paclobutrazol drenches were not economically feasible for reducing plant growth. Hard pruning to control plant size results in good regrowth.

Leaf/stems: Initial leaves on 'Prince' emerge with a purple midrib (187B on the adaxial side and 187A on the abaxial side) and a mottled mixture of purple (187C) and green (137B) blade. Later, the leaves emerge purple (187C) on both the adaxial and abaxial sides from the whorls. The leaf blade is flat, narrow, pointed at the end, sessile to the stem, and connected to the stem internode via the leaf sheath. The inside of the leaf collar is lined with abundant 2 mm long trichomes. There is bloom (155C) on the stems, abundant trichomes (1 to 2 mm long) on the sheath, trichomes (up to 4 mm long) 12 cm up the margin of the blade from the collar, and sparse trichomes (1 mm long) on the adaxial leaf surface. Margins of leaf blades have prominent trichomes (0.2 mm long). The abaxial leaf surface is smooth. Leaf color of both the adaxial and abaxial leaf surfaces best fits the greyed-purple group 187B.

The length of leaf ranges from 84 to 86 cm under different environmental conditions, with an average length of 84 cm. The leaf width ranges from 29 to 35 mm, with an average width of 31 mm.

Flowering: These plants flower under short days, less than 11 hours sunlight per day, and remain vegetative without producing inflorescences in the area of development and proposed use. Plants freeze due to cold temperatures before inflorescences are produced.

Plants are not recommended for landscape use in areas where a hard freeze does not regularly occur by December 1 (USDA 9–11) since reseeding may be an issue, particularly in humid, subtropical environments.

Diseases: Helminthosporium leaf spot has been noted on the foliage in the field and under overhead sprinklers in container nurseries, but control has not been necessary. Two-lined spittlebug (*Prosapia bicinta* (Say)) has also been noted to feed on the bases of field and container-grown plants. In the field, plants should be cut back in the late winter to remove debris that harbors spittlebugs.

We claim:

1. A new and distinct variety of *Pennisetum purpureum* plant, substantially as herein described and illustrated.

* * * * *